(12) United States Patent
Lim et al.

(10) Patent No.: US 8,455,018 B2
(45) Date of Patent: Jun. 4, 2013

(54) VISION-PROTECTING COMPOSITION WITH PROPHYLACTIC AND THERAPEUTIC ACTIVITY AGAINST DIABETES OR DIABETIC COMPLICATIONS

(75) Inventors: Beong Ou Lim, Chungcheongbukdo (KR); Khan O, Seoul (KR); Yun Hui Jeon, Gyeonggido (KR); Young Jun Jeoung, Gyeonggido (KR)

(73) Assignee: Konkuk University Industrial Cooperation, Seoul (KR)

( * ) Notice: Subject to any disclaimer, the term of this patent is extended or adjusted under 35 U.S.C. 154(b) by 0 days.

(21) Appl. No.: 13/143,466

(22) PCT Filed: Dec. 23, 2009

(86) PCT No.: PCT/KR2009/007732
§ 371 (c)(1),
(2), (4) Date: Jul. 6, 2011

(87) PCT Pub. No.: WO2010/079910
PCT Pub. Date: Jul. 15, 2010

(65) Prior Publication Data
US 2011/0268827 A1 Nov. 3, 2011

(30) Foreign Application Priority Data
Jan. 8, 2009 (KR) .................. 10-2009-0001356

(51) Int. Cl.
*A61K 36/00* (2006.01)
*A61K 36/482* (2006.01)
*A61K 36/8984* (2006.01)
*A61K 36/73* (2006.01)

(52) U.S. Cl.
USPC .......................... 424/725; 424/765; 424/777

(58) Field of Classification Search
None
See application file for complete search history.

(56) References Cited

U.S. PATENT DOCUMENTS

| 2005/0058730 | A1* | 3/2005 | Wan et al. ..................... 424/735 |
| 2005/0085454 | A1* | 4/2005 | Ghosal .......................... 514/185 |
| 2006/0079490 | A1* | 4/2006 | DeLuca et al. ................ 514/167 |
| 2008/0102137 | A1* | 5/2008 | Guffey .......................... 424/641 |
| 2008/0268066 | A1* | 10/2008 | Yie et al. ....................... 424/641 |

FOREIGN PATENT DOCUMENTS

| CN | 101371837 A | * | 2/2009 |
| KR | 10-0393908 B1 | | 8/2003 |
| KR | 2006023503 A | * | 3/2006 |
| KR | 2006025990 A | * | 3/2006 |
| KR | 10-2008-0088925 A | | 10/2008 |

OTHER PUBLICATIONS

H. J. Choi et al., "Effects of Polygonatum odoratum on In vivo Insulin Activity in Streptozotocin-Induced Diabetic Rats", The Korean Nutrition Society, 2003, pp. 239-244, vol. 36, No. 3.
M. B. Gomes et al., "Acute-phase proteins and microalbuminuria among patients with type 2 diabetes", Diabetes Research and Clinical Practice, 2004, pp. 31-39, vol. 66.
K. E. Izuora et al., "Inflammatory Markers and Diabetic Retinopathy in Type 1 Diabetes", Diabetes Care, 2005, pp. 714-715, vol. 28, No. 3.
B. S. Jung et al., "Illustrated encyclopedia of Korean Medicinal Herbs", Seoul, Younglim Press, 2003, pp. 663-664, ISBN 89-85897-04-7 91510.
K. S. Kim et al., "Anti-diabetic Activity of Constituents of Lycii Fructus", The Journal of Applied Pharmacology, 1998, pp. 378-382, vol. 6.
K. W. Lee et al., "The change of prevalence of diabetes mellitus for 3 years and incidence of diabetes in Koreans over 60 years old", Journal of Korean Internal Medicine, 2004, pp. 607-615, vol. 67, No. 6.
S. Liekens et al., "Angiogenesis: regulators and clinical applications", Biochemical Pharmacology, 2001, pp. 253-270, vol. 61.
S. J. Lim et al., "Hypoglycemic Effect of Fractions of Cassia tora Extract in Streptozotocin-Induced Diabetic Rats", Korean Journal of Food and Cookery Science, 1997, pp. 23-29, vol. 13, No. 1.
Peter R. Shepherd et al., "Glucose transporters and insulin action", The New England Journal of Medicine, 1999, pp. 248-257, vol. 341.
American Diabetes Association, "Diagnosis and Classification of Diabetes Mellitus", Diabetes Care, 2004, pp. S5-S10, vol. 27, No. 1.
English Language Abstract of KR 10-2002-0061902 A which is the application publication of KR 10-0393908 B1.
English Language Abstract of KR 10-2008-0088925 A.
International Search Report of PCT/KR2009/007732 mailed on Aug. 13, 2010.

* cited by examiner

*Primary Examiner* — Qiuwen Mi
(74) *Attorney, Agent, or Firm* — Rabin & Berdo, P.C.

(57) ABSTRACT

A vision-protecting composition with prophylactic and therapeutic activity of diabetes or diabetic complications, comprising calcium, vitamin A, vitamin B, vitamin C and vitamin D as functional ingredients, in combination with at least one herb extract selected from the group consisting of a wolfberry extract, an *Astragalus membranaceus* extract, a *Senna obtusifolia* extract, a *Polygonatum odoratum* var. *pluriflorum* extract and a *Rubus coreanus* extract. Found to be significantly suppressive and regulatory of the expression of inflammatory factors, the cytokine expression of Th1/Th2 cells via the JAK-STAT signaling pathway, and the expression of STAT3 in diabetic retinopathy, the composition can be used to protect vision as well as for the prophylaxis or treatment of diabetes and diabetic complications.

6 Claims, 8 Drawing Sheets

VISION-PROTECTING COMPOSITION WITH PROPHYLACTIC AND THERAPEUTIC ACTIVITY AGAINST DIABETES OR DIABETIC COMPLICATIONS

CROSS-REFERENCE TO RELATED APPLICATIONS

This application is the National Stage of PCT/KR09/07732 filed on Dec. 23, 2009, which claims foreign priority under 35 U.S.C. §119 of Republic of Korean 10-2009-0001356 filed on Jan. 8, 2009, which are hereby incorporated by reference in their entirety.

BACKGROUND OF THE INVENTION

1. Field of the Invention

The present invention relates to a vision-protecting composition with prophylactic and therapeutic activity for diabetes or diabetic complications. More particularly, the present invention relates to a vision-protecting composition with prophylactic and therapeutic activity against diabetes or diabetic complications, comprising calcium, vitamin A, vitamin B, vitamin C and vitamin D and optionally a herb extract selected from among a wolfberry extract, an *Astragalus membranaceus* extract, a *Senna obtusifolia* extract, a *Polygonatum odoratum* var. *pluriflorum* extract, a *Rubus coreanus* extract and a combination thereof.

2. Description of the Related Art

Diabetes mellitus is one of the most prevalent chronic adult diseases. With the improvement of standards of living and the Westernization of dietary habits, the onset of diabetes has become increasingly prevalent in Korea. In the body, control of the sugar metabolism resides in a balance between consumption and production of sugar in which insulin and glucagon are typically known to be involved. Depending on these hormones, blood sugar levels vary within certain ranges. Any abnormal action of these hormones leads to a problem with sugar metabolism, typically such as diabetes mellitus (Shepherd P R, Kahn B B: Glucose transporters and insulin action-implications for insulin resistance and diabetes mellitus. *N Engl J Med* 341: 248-257, 1999).

Diabetes mellitus is a group of metabolic diseases characterized by hyperglycemia resulting from the absolute or relative deficiency of insulin activity. The chronic hyperglycemia of diabetes with the poor regulation of blood sugar is associated with long-term complications including hyperlipidemia, retinopathy, nephropathy and nephrotoxicity, which may even result in death. (American Diabetes Association: Diagnosis and classification of diabetes mellitus. *Diabetes Care* 27: S5-S10, 2004).

Diabetic retinopathy, a complication of diabetes, is a cause of the loss of vision in adults. Due to an impairment of the blood-retinal barrier with microvascular retinal changes, diabetic retinopathy may progress into proliferative diabetic retinopathy, which can eventually lead to blindness. Active research has been directed toward diabetic retinopathy. Angiogenesis plays an important role in the development of proliferative diabetic retinopathy. In the complex processes of angiogenesis, various kinds of cytokines to and growth factors are involved as previously reported (Lee K W, Kim D J, Park J R et al., *J Korean Internal Medicine* 67: 607-615, 2004; Liekens S et at, *Biochemi Pharmacol* 61: 253-270, 2001). In a hypertensive condition induced by diabetes mellitus, a variety of cells are promoted to secrete inflammatory factors, with the induction of lipocytes to form and secrete acute reactive factors. High blood sugar and its oxides cause damage to the eyes, the kidneys and vascular cells and the inflammatory factors penetrate into the damaged regions, thus causing damage to more cells. The role of inflammatory factors in the development of complications of diabetes is already known. Recent reports had it that inflammatory factors are associated with the onset of microvascular complications such as microalbuminuria and diabetic retinitis, as well as macrovascular complications such as cardiovascular diseases (Gomes M B, Nogueira V G, *Diabetes Research and Clinical Practice* 66: 31-39, 2004; Kenneth E. et al., *Diabetes Care* 28: 714-715, 2005).

T helper cells function to regulate and activate a variety of immune responses. Proliferating helper T cells that develop into effector T cells differentiate into Th1 and Th2 cells. They express their characteristic cytokines that are responsible for different immune functions. Immune homeostasis may be defined as a balance between Th1 and Th2 cells. The onset of a certain immune disease is such that the immune imbalance incurred with the collapse of Th1/Th2 balance induces immune diseases of each T helper type. Inadequate Th1 immune responses account for autoimmune diseases such as rheumatoid and diabetes while hypersensitive Th2 immune responses result in allergy and asthma.

On the basis of accurate understanding of the etiology and pathophysiology of diabetes mellitus, molecular biological studies have recently been actively performed to develop improved therapeutics overcoming the limitations of conventional ones. Against the background of these studies, various transcription factors are suggested as theoretical bases for the development of new drugs. In practice, research results have been reported that have focused on immunoregulators, inflammatory factors, growth factors, cytokines and the like. In addition, complications of diabetes mellitus, rather than diabetes mellitus itself, are under active study because they are more serious in many cases (Jeon, Young Jin, The Korean Society for Microbiology and Biotechnology, Trends of Research into Complications of Diabetes Mellitus, Pharmacology Class, College of Medicine, Chosun University).

However, a velar interrelationship has to be proven between various signal transmitters, growth factors, cytokines, immune regulators, and inflammatory factors in the abnormality of sugar metabolisms and the onset of diabetes and diabetic complications. Particularly, studies on diabetic retinopathy remain only slightly advanced.

SUMMARY OF THE INVENTION

Leading to the present invention, intensive and thorough research into the effects of various functional ingredients on diabetes-related cytokines, immune regulators and inflammatory factors, conducted by the present invention resulted in the finding that certain herb extracts, in combination with calcium and vitamins, can regulate the expression of diabetes-related inflammatory factors and immune regulators and can significantly inhibit the onset of diabetic retinopathy.

It is therefore an object of the present invention to provide a vision-protecting composition prophylactic or therapeutic for diabetes or diabetic complications.

The above object could be accomplished by a provision of a vision-protecting composition prophylactic and therapeutic for diabetes or diabetic complications, comprising calcium, vitamin A, vitamin C, vitamin B and vitamin D as functional ingredients, in combination with an extract from at least one herb selected from the group consisting of wolfberry, *Astragalus membranaceus*, *Senna obtusifolia*, *Polygonatum odoratum* var. *pluriflorum*, and *Rubus coreanus*.

In an embodiment, the calcium useful in the present invention is seaweed calcium. In another embodiment of the present invention the vitamin B may be selected from the group consisting of vitamins B1, B2, B3, B6, B12 and a combination thereof, and preferably is a combination of vitamins B1, B2, B3, B6 and B12. The vitamin D may be vitamin D3.

Based on 100 wt % of the composition of the present invention, calcium may be contained in an amount of from 4 to 10 wt %, vitamin A in an amount of from 0.001 to 0.1 wt %, vitamin C in an amount of from 0.1 to 1 wt %, vitamin B in an amount of from 0.0001 to 0.1 wt %, and vitamin D in an amount of from 0.001 to 0.5 wt %.

As for the vitamin B, it may comprise vitamin B1 in an amount of 0.0003 wt %, vitamin B2 in an amount of 0.0005 wt %, vitamin B3 in an amount of 0.001 wt %, vitamin B6 in an amount of 0.001 wt %, and vitamin B12 in an amount of 0.0001 wt % based on 100 wt % of the composition.

In accordance with the present invention, the herb extract is contained in an amount of from 0.1 to 5 wt % based on 100 wt % of the composition. Preferably, the herb extract may comprise 30 wt % of a wolfberry extract, 27 wt % of an *Astragalus membranaceus* extract, 25 wt % of a *Senna obtusifolia* extract, 10 wt % of a *Polygonatum odoratum* var. *pluriflorum* extract, and 8 wt % of a *Rubus coreanus* extract.

Found to be significantly suppressive and regulatory of the expression of inflammatory factors, the cytokine expression of Th1/Th2 cells via the JAK-STAT signaling pathway, and the expression of STAT3 in diabetic retinopathy, the composition of the present invention can be used to protect vision as well as for the prophylaxis or treatment of diabetes and diabetic complications.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

The present invention contemplates a vision-protecting composition prophylactic and therapeutic of diabetes or diabetic complications, comprising calcium, vitamin A, vitamin B, vitamin C and vitamin D as functional ingredients, in combination with at least one herb extract selected from a wolfberry extract, an *Astragalus membranaceus* extract, a *Senna obtusifolia* extract, a *Polygonatum odoratum* var. *pluriflorum* extract and a *Rubus coreanus* extract.

As used herein, the term "functional ingredient" is intended to refer to an ingredient useful in the prevention or treatment of diabetes or diabetic complications. In the present invention, the functional ingredients account for calcium, vitamin A, vitamin B, vitamin C and vitamin D.

In accordance with the present invention, calcium may be seaweed calcium (water-soluble aquamine, non-sintered, with a calcium content of 12% or higher) or a calcium salt of a fermented organic acid (non-sintered, a calcium content of 13% or higher) and is contained in an amount of from 4 to 10 wt % based on 100 wt % of the composition.

The vitamin A is contained in an amount of from 0.001 to 0.1 wt % based on 100 wt % of the composition.

The vitamin B used in the present invention is selected from the group consisting of vitamin B1, B2, B3, B6, B12 and a combination thereof and preferably a combination of vitamin B1, B2, B3, B6 and B12. It is used in an amount of from 0.0001 to 0.1 wt % based on 100 wt % of the composition. Preferably, the composition comprises vitamin B1 in an amount of 0.0003 wt %, vitamin B2 in an amount of 0.0005 wt %, vitamin B3 in an amount of 0.001 wt %, vitamin B6 in an amount of 0.001 wt %, and vitamin B12 in an amount of 0.0001 wt %.

The vitamin D may be vitamin D3 and is contained in an amount of from 0.001 to 0.5 wt % and the vitamin C is used in an amount of from 0.1 to 1 wt %.

As used herein, the term "herb extract" is intended to refer to an extract from a herb, obtained using a typical extraction method, or an extract commercially available in the form of powder. Preferably, it is at least one selected from the group consisting of a wolfberry extract, an *Astragalus membranaceus* extract, a *Senna obtusifolia* extract, a *Polygonatum odoratum* var. *pluriflorum* extract, and a *Rubus coreanus* extract.

The herb extract is contained in an amount of from 0.1 to 5 wt %, based on 100 wt % of the composition and is preferably comprised of 30 wt % of a wolfberry extract, 27 wt % of an *Astragalus membranaceus* extract, 25 wt % of a *Senna obtusifolia* extract, 10 wt % of a *Polygonatum odoratum* var. *pluriflorum* extract, and 8 wt % of a *Rubus coreanus* extract.

As will be illustrated in the following Example section, the composition of the present invention significantly inhibits or regulates the expression of inflammatory factors, regulating the cytokine expression of Th1/Th2 cells via the JAK-STAT signaling pathway and the expression of STAT3 in diabetic retinopathy so that it can be useful for the prevention and treatment of diabetes or diabetic complications.

Also, the vision-protecting composition prophylactic and therapeutic of diabetes or diabetic complications in accordance with the present invention may further comprise a pharmaceutically acceptable vehicle.

The composition of the present invention may be used alone or in combination with a pharmaceutically acceptable vehicle or excipient depending on its use, and may take any dosage form so long as it is suitable for administration to humans. Constituents useful in the composition of the present invention may include a thickener, dietary fiber, a capsulation agent, lipid, and so forth, and are well known in the art.

Depending on a variety of factors including the severity of disease, the age, gender, body state, weight, and diet of patients, the time of administration, the mode of administration, and the rate of excretion, the suitable dosage of the pharmaceutical composition of the present invention will vary.

Preferably, the composition of the present invention is administered once a day for a desired effect. However, the time of administration limits the present invention in no way.

A better understanding of the present invention may be obtained through the following examples which are set forth to illustrate, but are not to be construed as limiting the present invention.

EXAMPLE 1

Preparation of Composition

Materials that satisfy official standards such as the Korean Health Functional Foods Codex, the Korean Food Standards Codex and the Korean Food Additives Codex were purchased, weighed, mixed and dissolved at 90° C. for 20 min in purified water in a tank with stirring. The resulting solution was filtered through a 10 microfilter and subjected to HTST sterilization to afford a composition, named I&H. The materials of the composition of the present invention are listed together their amounts in Table 1, below.

TABLE 1

| Material | Amount (wt %) |
|---|---|
| Seaweed Calcium | 4.375 |
| Fermented organic acid calcium | 4.050 |
| High fructose corn syrup | 25 |
| Blueberry concentrate | 1 |
| Herb extract mix V-1 | 1 |
| Pectin | 1 |
| vitamin C (L-Ascorbic acid) | 0.5 |
| vitamin A acetate | 0.021 |
| Sucralose | 0.02 |
| Magnesium chloride | 0.01 |
| Astaxanthin | 0.01 |
| vitamin B3 | 0.001 |
| vitamin B6 | 0.001 |
| vitamin B1 chloride | 0.0003 |
| Purified Water | 61.4998 |
| DL-alanine | 0.4 |
| Red dye | 0.35 |
| Blueberry flavor | 0.35 |
| Gelling agent | 0.2 |
| Colostrum powder | 0.1 |
| Marigold extract powder | 0.05 |
| Milk protein hydrolysate | 0.03 |
| vitamin D3 | 0.01 |
| Beta carotene | 0.01 |
| Rutin | 0.01 |
| Zinc oxide | 0.001 |
| vitamin B2 | 0.005 |
| Folic acid | 0.0003 |
| vitamin B12 | 0.0001 |

The herb extract mix V-1 was comprised of wolfberry extract 30 wt %, *Astragalus membranaceus* extract 27 wt %, *Senna obtusifolia* extract 25 wt %, *Polygonatum odoratum* var. *pluriflorum* extract 10 wt % and *Rubus coreanus* extract 8 wt %.

EXPERIMENTAL EXAMPLE 1

Measurement of Weight Change

Sprague-Dawely rats weighing 140-230 g, purchased from Orient Bio Inc. (Sungnam Korea), were acclimated to an experimental environment for one week, with free access to feeds and water (temperature of 22.2° C., humidity of 55-66%, dark/light cycles of 12/12 h) before an experiment.

The rats were divided into four groups of seven according to randomized block design so that average body weights were similar among the groups, and were used as a normal control, a diabetes control (STZ group) in which diabetes were induced by streptozotocin (STZ), an STZ+I&H group in which the inventive composition I&H was administered into streptozotocin-induced diabetic rats, and an I&H group in which the inventive composition I&H was administered to normal rats, respectively. After the experiment of four weeks, the experimental animals were monitored for their weight change and the results are depicted in FIG. 1.

Figure 1:
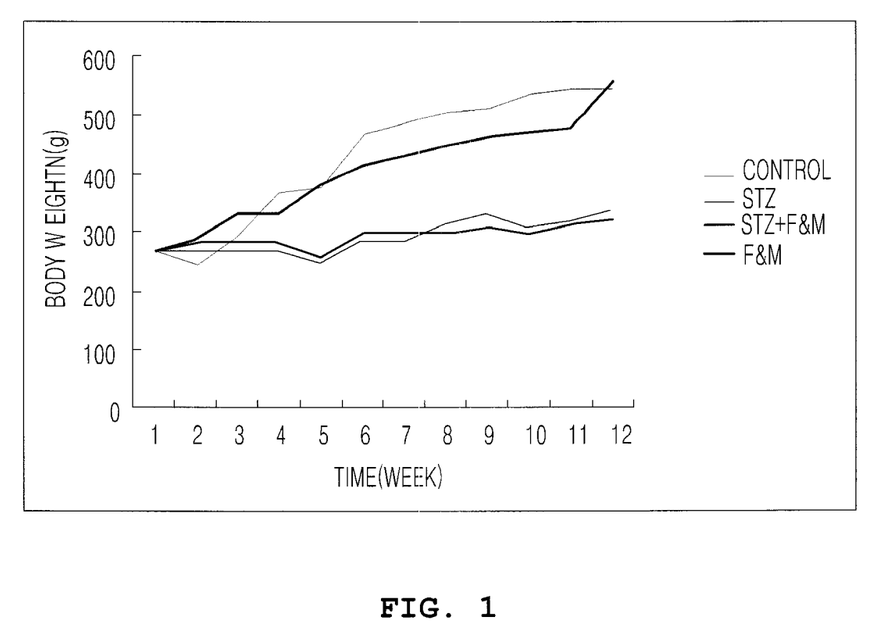
FIG. 1 is a graph showing changes in body weight of rats with administration of the inventive composition (I&H)

As seen in FIG. 1, all of the experimental animals were observed to slightly change in body weight.

EXPERIMENTAL EXAMPLE 2

Induction of Diabetes by Streptozotocin

Streptozotocin-induced diabetes was achieved according to the method of Cho et al. (Cho Y. J., Bang M. A., Hypoglycemic and Antioxidative Effects of Dietary Sea-Tangle Extracts Supplementation in Streptozotocin-Induced Diabetic Rats, *The Korean Nutrition Society*, 37(1): 5-14, 2004).

In detail, male rats four weeks old were intraperitoneally injected with streptozotocin at a dose of 60 mg per kg to induce diabetes therein, and were bred for four weeks. Thereafter, the rats were starved for 12 hours and then opened at their abdomen under ether anesthesia. Whole blood samples were taken from the hepatic portal vein and centrifuged to remove sera as supernatants. Separately, the spleen, the liver and the retinal lenses were excised, frozen in liquid nitrogen and stored at −70° C. before use.

In Table 2, below, the weight measurements of the liver and the spleen after breeding of four weeks are listed. Table 3 shows the incidence rates of cataract in the anterior chamber of the eye with the lapse of time after the induction of diabetes by streptozotocin.

In the case of the spleen, as can be seen in Table 2, a significant increase was observed in the diabetes control (STZ), but decrease in the groups administered with the composition of the present invention (STZ+I&H, I&H). Also, similar results were found as to the liver. Particularly, a significant to decrease was detected in the STZ+I&H group.

These results indicate that the inventive composition reduces burdens imparted to the spleen and the liver of diabetic animal models and is involved in the improvement of glucose metabolism.

As seen in Table 3, cataract was understood to come from the streptozotocin-induced diabetes as it was spread over the anterior chamber of the eye.

TABLE 2

|  | Liver | Spleen |
|---|---|---|
| Normal control | 14.67 ± 3.779 | 0.715 ± 0.275 |
| STZ | 10.831 ± 3.75 | 0.286 ± 0.15 |
| STZ + I&H | 11.171 ± 1.626 | 0.327 ± 0.13 |
| I&H | 13.963 ± 4.604 | 0.718 ± 0.213 |

Values expressed as mean±standard deviation.

TABLE 3

| | 1st | 2nd | 3rd | Final |
|---|---|---|---|---|
| Normal control | 86.5 | 92.2 | 109.2 | 222.6 |
| STZ | 132.9 | 172.5 | 239.8 | 489 |
| STZ + I&H | 116.9 | 124.1 | 285.4 | 477 |
| I&H | 84 | 89.2 | 110.2 | 184.9 |

EXPERIMENTAL EXAMPLE 3

Measurement of Blood Glucose

Blood glucose levels (mg/dl) were measured using a blood sugar meter (Care Sens II, I Sens, Kora). Blood was sampled from the tail vein.

Figure 2:
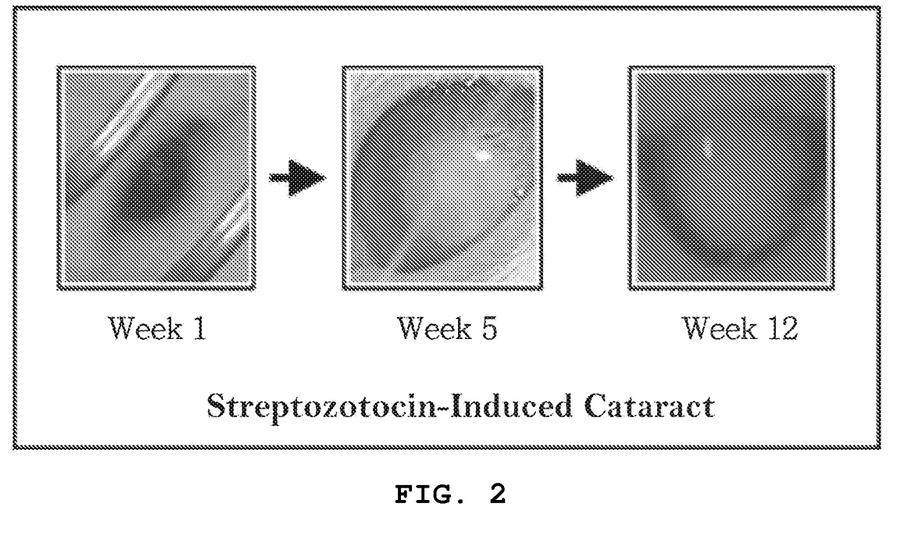
FIG. 2 is a view showing changes in blood glucose levels of rats with administration of the inventive composition (I&H)

The results are shown in FIG. 2. As seen in FIG. 2, blood glucose levels were significantly increased in the STZ group, compared tp the normal control, but decreased in the STZ+I&H group. Particularly, a significant decrease in blood glucose level was observed in the I&H group, compared to the control.

From these results, it is understood that the composition of the present invention is effective for decreasing blood glucose levels.

EXPERIMENTAL EXAMPLE 4

Assay for Activity to Regulating Inflammation, Immune Response and Retinopathy

Expression levels of TNF-α, INF-γ, STAT1, pSTAT1, JAK1, T-bet, IL-12p35, IL-12p40, STAT4, IL-4, STAT6, pSTAT6, GATA3, IL-6, STAT3, and pSTAT3 were measured using Western blotting.

In detail, after being excised, the spleen and the liver were placed in 500 μL of lysis buffer (150 mM NaCl, 1% NP40, 0.5% deoxycholic acid, 0.1% sodium Dodecyl salfate, 50 mM Tris, 1 tablet/20 mL protease inhibitor) and left for 10 min on ice. After centrifugation at 12,000 rpm for 20 min, the proteins dissolved in the buffer were obtained and quantitatively analyzed using a BSA protein assay kit. Each protein was mixed with an SDS sample buffer (4% SDS, 20% glycerol, 0.2% bromophenol blue, 2.8% 2-mercaptoethanol, 125 mM Tris-HCl pH6.8) and separated in 8%, 10%, 12% or 15% SDS-PAGE gel by electrophoresis. The proteins were transferred from the gel to a nitrocellulose membrane for use in immune-blotting. To prevent non-specific reactions thereon, the nitrocellulose membrane was block for 60 min with 5% skim milk in TBS-T (0.5M NaCl, 20 mM Tris-HCl pH7.2 0.2% tween20), and washed six times for 5 min with TBS-T (0.5M NaCl, 20 mM Tris-HCl pH7.2, 0.2% tween20). Thereafter, the membrane was incubated overnight with 1 μg/ml of a primary antibody in TBS-T containing 1 mg/mL BSA and then washed six times for 5 min with TBS-T. Afterwards, the membrane was incubated for one hour with a secondary antibody diluted at 1:1000 in TBS-T with 2% skim milk and washed six times for five minutes with TBS-T, followed by development using a 1:1 dilution of ECL. Expression levels of the proteins of interest were determined.

To identify the onset of cataract and retinopathy in the diabetes-induced rats and to assay the composition for inhibitory activity against the diseases, ocular lenses were subjected to Western blot analysis, as described above, to determine the expression levels of IL-6, STAT3, iNOS, and TNF-α.

The results are shown in FIGS. 3 to 8.

Figure 3:
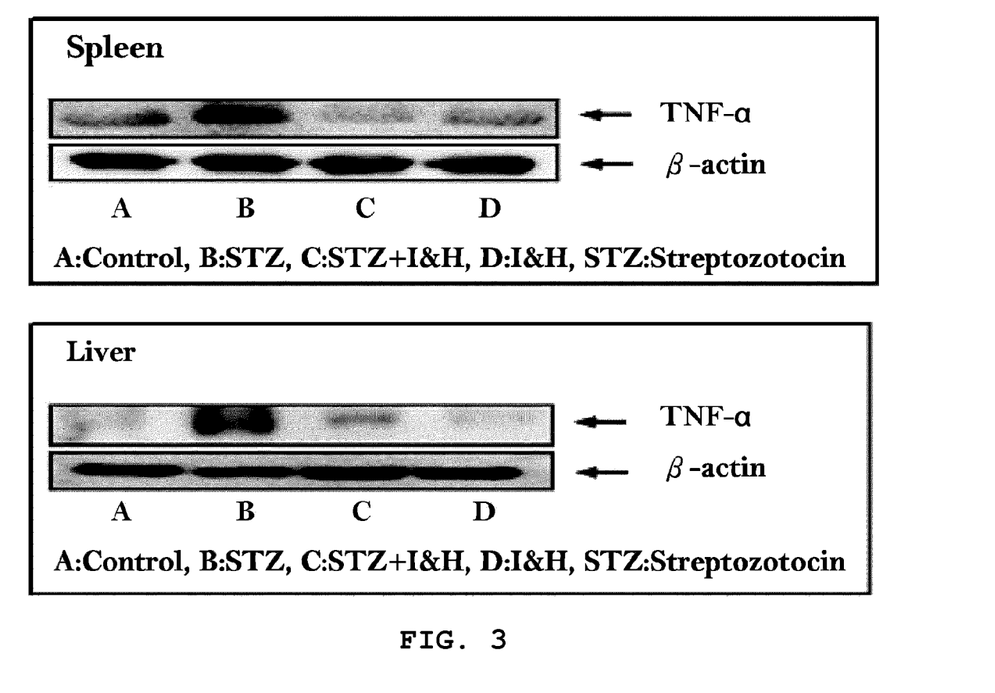
FIG. 3 shows expression levels of TNF-α, in the spleens and the livers of rats administered with the inventive composition (I&H)

As can be seen in FIG. 3, TNF-α was highly expressed in the STZ group, but was detected at a significantly low level in the STZ+I&H group, which indicates that the composition of the present invention has the activity of suppressing the expression of TNF-α and thus inflammation.

Figure 4:
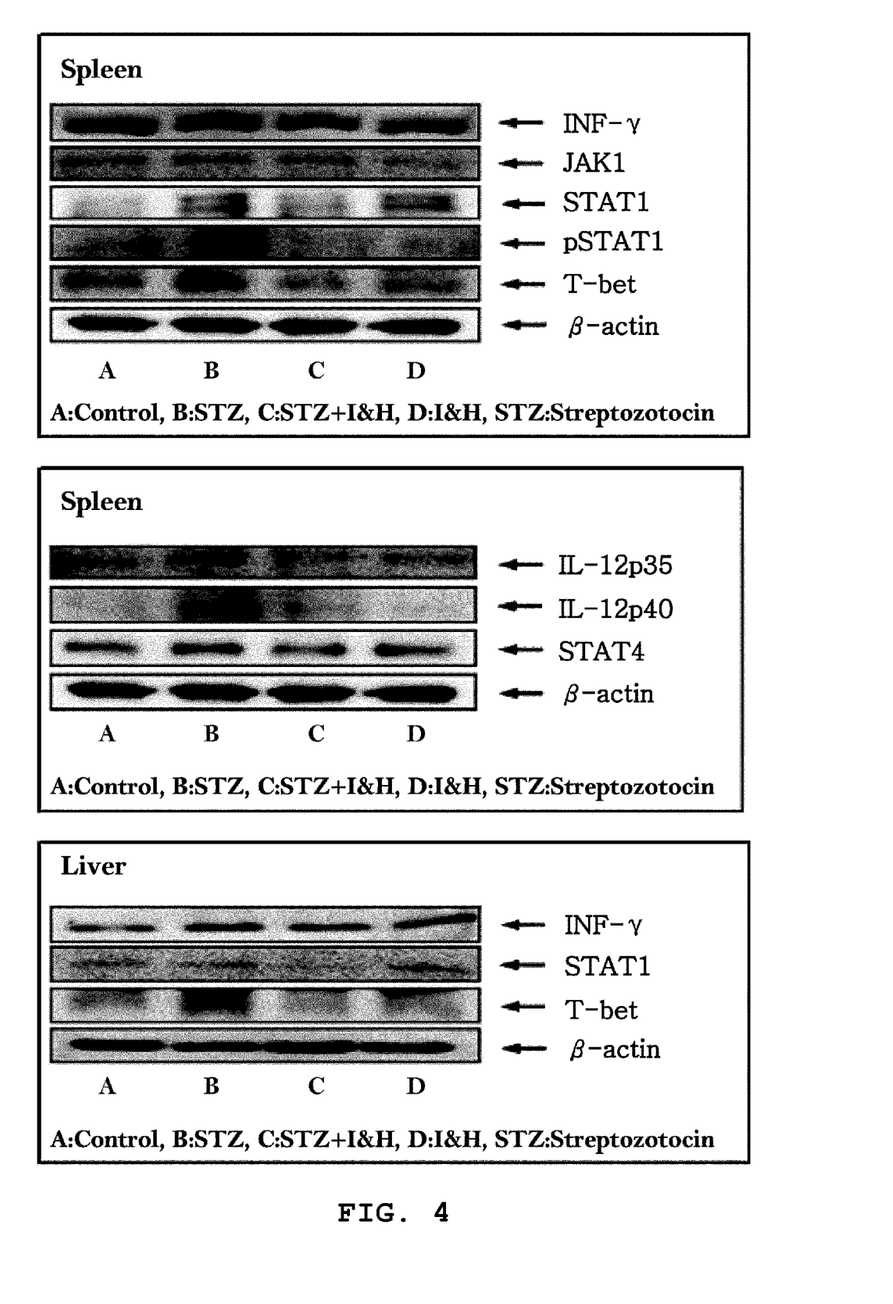
FIG. 4 shows expression levels of Th1 cell-regulating cytokines (IFN-γ pathway) in the spleens and the livers of rats administered with the inventive composition (I&H)
Figure 5:
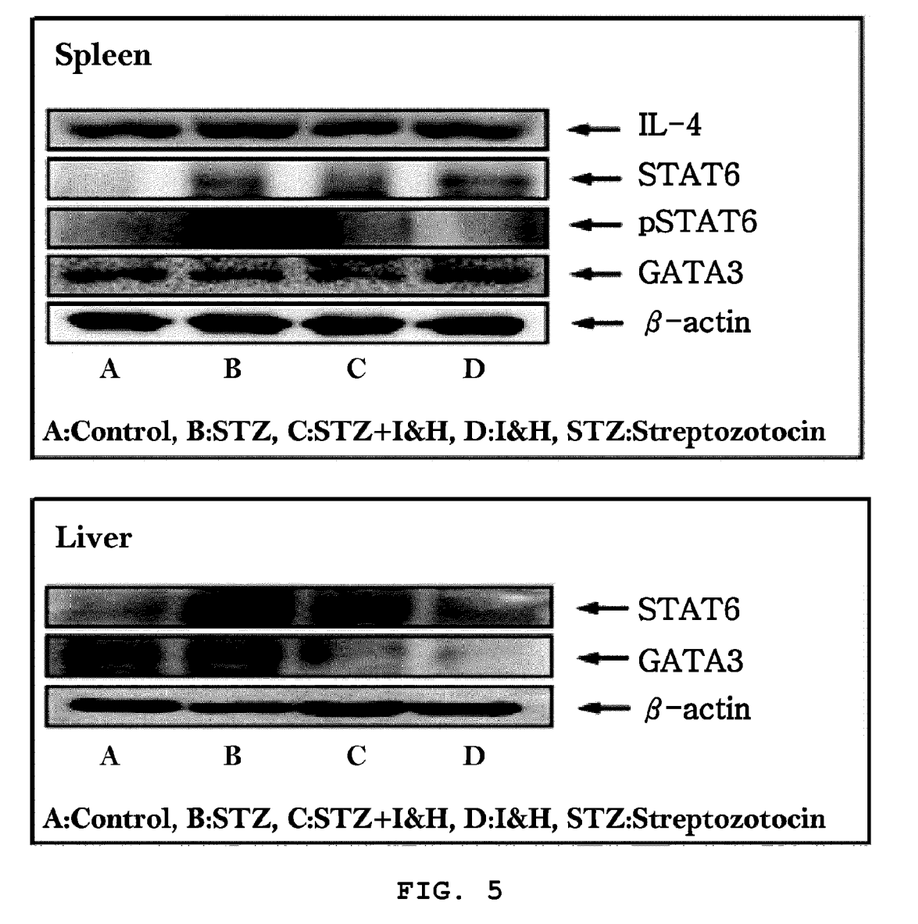
FIG. 5 shows expression levels of Th2 cell-regulating cytokines (IL-4 pathway in the spleens and the livers of rats administered with the inventive composition (I&H)
Figure 6:
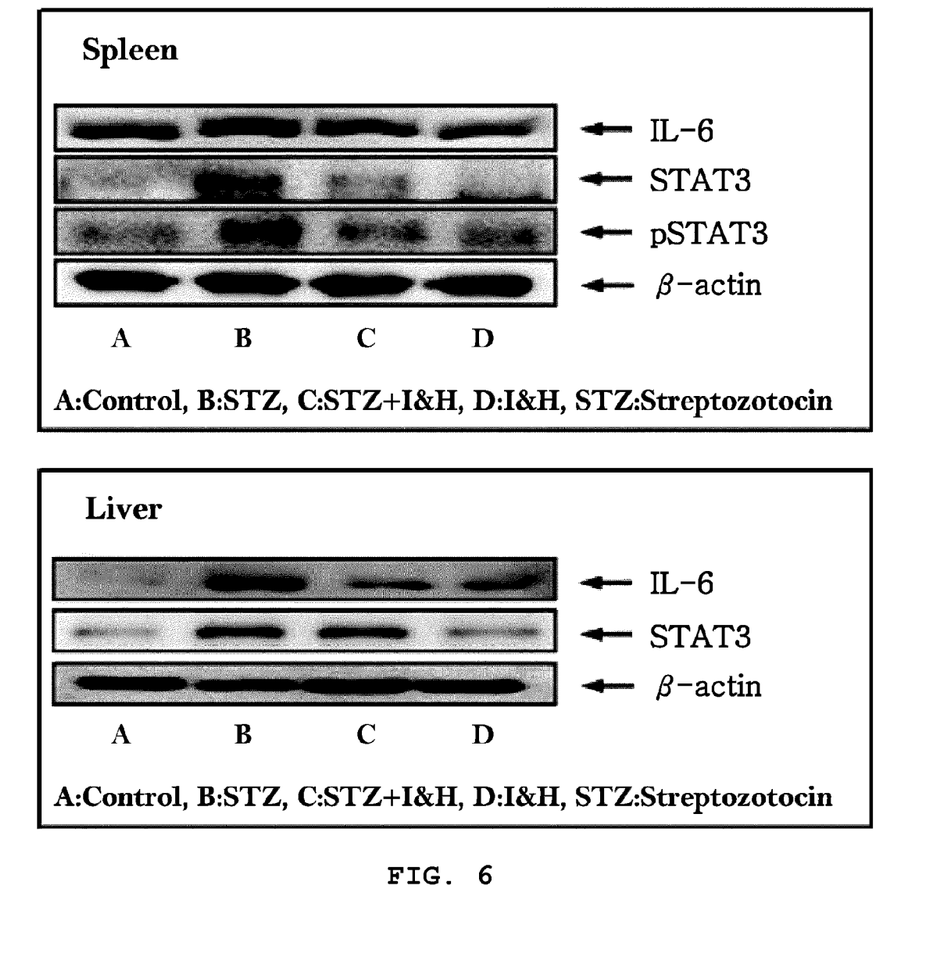
FIG. 6 shows expression levels of IL-6-mediated cytokines in the spleens and the livers of rats administered with the inventive composition (I&H)

Also, as seen in FIGS. 4 to 6, the JAK-STAT-mediated cytokine expression of Th1/Th2 cells was remarkably increased in the STZ group, but decreased in the STZ+I&H group. These results demonstrate that the composition of the present invention can suppress and regulate the cytokine expression of Th1/Th2 cells via the JAK-STAT signaling pathway and play a role in balancing between Th1 and Th2 cell-mediated immune responses, contributing to achieving an immune balance. In addition, as a significant result was obtained in the regulation of IL-6 and STAT3, which is associated with glucose metabolism, the composition of the present invention was understood to have a positive influence on glucose metabolism.

Figure 7:
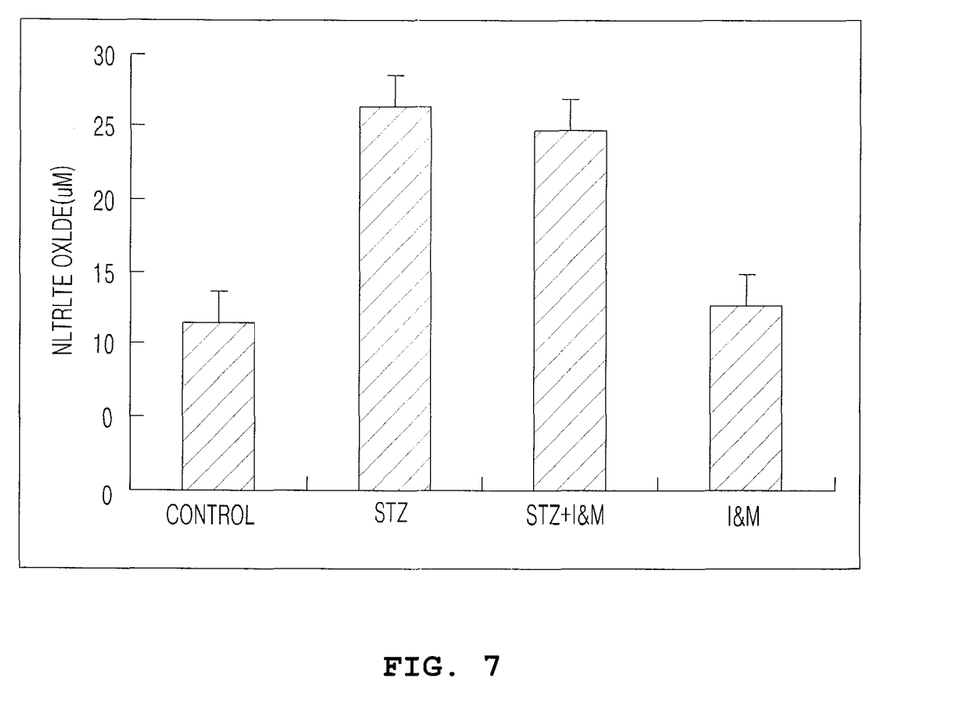
FIG. 7 shows the production levels of nitrogen oxide in the retina of rats administered with the inventive composition (I&H)
Figure 8:
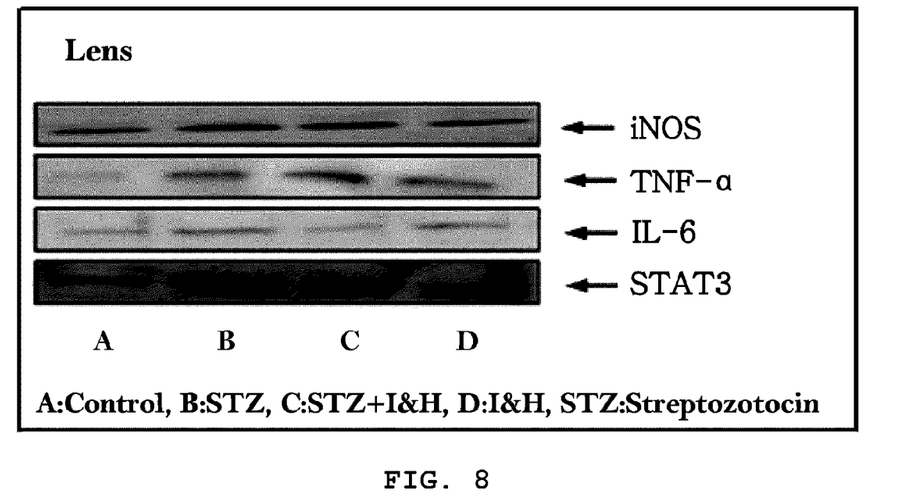
FIG. 8 shows the expression levels of iNOS, TNF-α, IL-6, and STAT3 in the retina of rats administered with the inventive composition (I&H).

As seen in FIGS. 7 and 8, cataract was observed to develop in the STZ group as the expression levels of cytokines responsible for inflammation and retinopathy were increased. In contrast, the expression levels were significantly reduced in the STZ+I&H group. STAT3, closely associated with the regulation of vascular endothelial growth factor, and its upstream regulator IL-6 were also significantly reduced in activity when the STZ group was administered with the inventive composition I&H.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A vision-protecting composition with therapeutic activity of diabetic cataract or diabetic retinopathy, comprising calcium, vitamin A, a mixture of vitamins B1, B2, B3, B6 and B12, vitamin C and vitamin D3 as functional ingredients, and a herb extract consisting of a wolfberry extract, an *Astragalus membranaceus* extract, a *Senna obtusifolia* extract, a *Polygonatum odoratum* var. *pluriflorum* extract and a *Rubus coreanus* extract.

2. The vision-protecting composition of claim 1, wherein the calcium is a mixture of seaweed calcium and a calcium salt of fermented organic acid.

3. The vision-protecting composition of claim 1, wherein the composition contains calcium in an amount of from 4 to 10 wt %, vitamin A in an amount of from 0.001 to 0.1 wt %, a mixture of vitamins B1, B2, B3, B6 and B12 in an amount of from 0.0001 to 0.1 wt %, vitamin C in an amount of from 0.1 to 1 wt %, and vitamin D3 in an amount of from 0.001 to 0.5 wt %, based on 100 wt % of the compostion.

4. The vision-protecting composition of claim 1, wherein the mixture of vitamins B1, B2, B3, B6 and B12 is composed of 0.0003 wt %wt % of vitamin B1, 0.0005 wt % of vitamin B2, 0.001 wt % of vitamin B3, 0.001 wt % of vitamin B6, and 0.0001 wt % of vitamin B12 based on 100 wt % of the composition.

5. The vision-protecting composition of claim 1, wherein the herb extract is contained in an amount of from 0.1 to 5 wt % based on 100 wt % of the composition.

6. The vision-protecting composition of claim 1, wherein the herb extract is composed of 30 wt % of a wolfberry extract, 27 wt % of an *Astragalus membranaceus* extract, 25 wt % of a *Senna obtusifolia* extract, 10 wt % of a *Polygonatum*

*odoratum* var. *pluriflorum* extract, and 8 wt % of a *Rubus coreanus* extract, based on 100 wt % of the herb extract.

\* \* \* \* \*